United States Patent [19]

Lammers

[11] Patent Number: 4,634,482
[45] Date of Patent: Jan. 6, 1987

[54] METHOD FOR SECURING ELASTIC STRANDS TO DISPOSABLE ABSORBENT ARTICLES

[75] Inventor: Donald W. Lammers, Oostburg, Wis.

[73] Assignee: Curt G. Joa, Inc., Sheboygan Falls, Wis.

[21] Appl. No.: 746,838

[22] Filed: Jun. 20, 1985

[51] Int. Cl.⁴ .............................................. B32B 31/08
[52] U.S. Cl. ........................... 156/164; 156/229; 156/291
[58] Field of Search .............. 156/164, 161, 163, 229, 156/176, 178, 179, 291

[56] References Cited

U.S. PATENT DOCUMENTS

| | | | |
|---|---|---|---|
| 4,081,301 | 3/1978 | Buell | 156/164 |
| 4,300,967 | 11/1981 | Sigl | 156/164 |
| 4,353,762 | 10/1982 | Bouda | 156/229 |
| 4,360,398 | 11/1982 | Sabee | 156/164 |

*Primary Examiner*—Michael Ball
*Attorney, Agent, or Firm*—Fuller, House & Hohenfeldt

[57] ABSTRACT

Stretched elastic strands and a continuous sheet are fed concurrently toward a diaper assembly station on the way to which quick setting adhesive is applied periodically to zones in one and slower setting adhesive is applied alternately periodically zones in the other. Diapers assembled as a continuous web at the station are ultimately severed at which time the quick setting adhesive zones are set already and impart elasticity to the crotch region of the diapers. The zones on the strands that are tentatively adhered to the sheet with slow setting adhesive contract gradually into the diaper along the straight adhesive lines and then they set.

7 Claims, 7 Drawing Figures

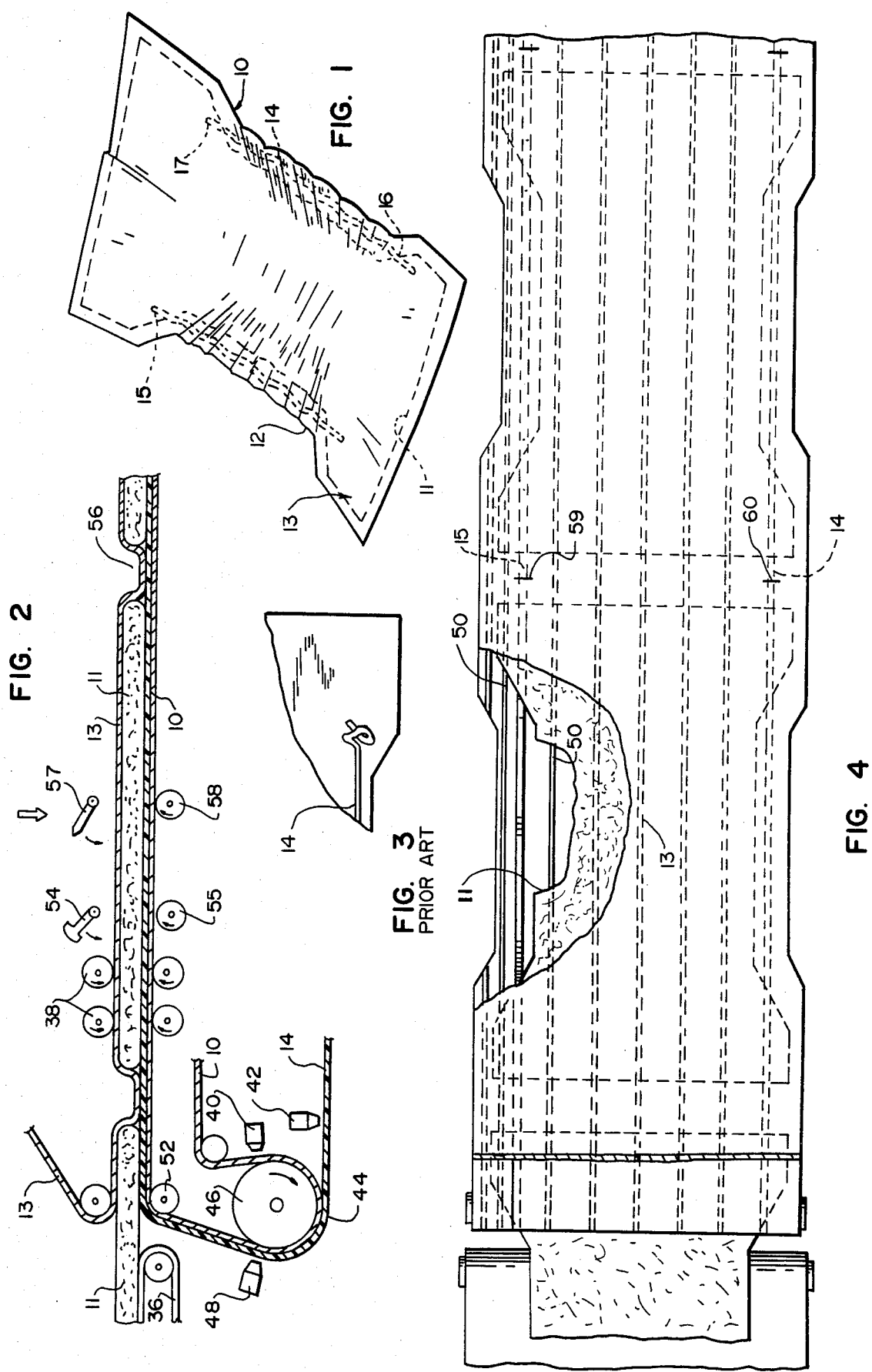

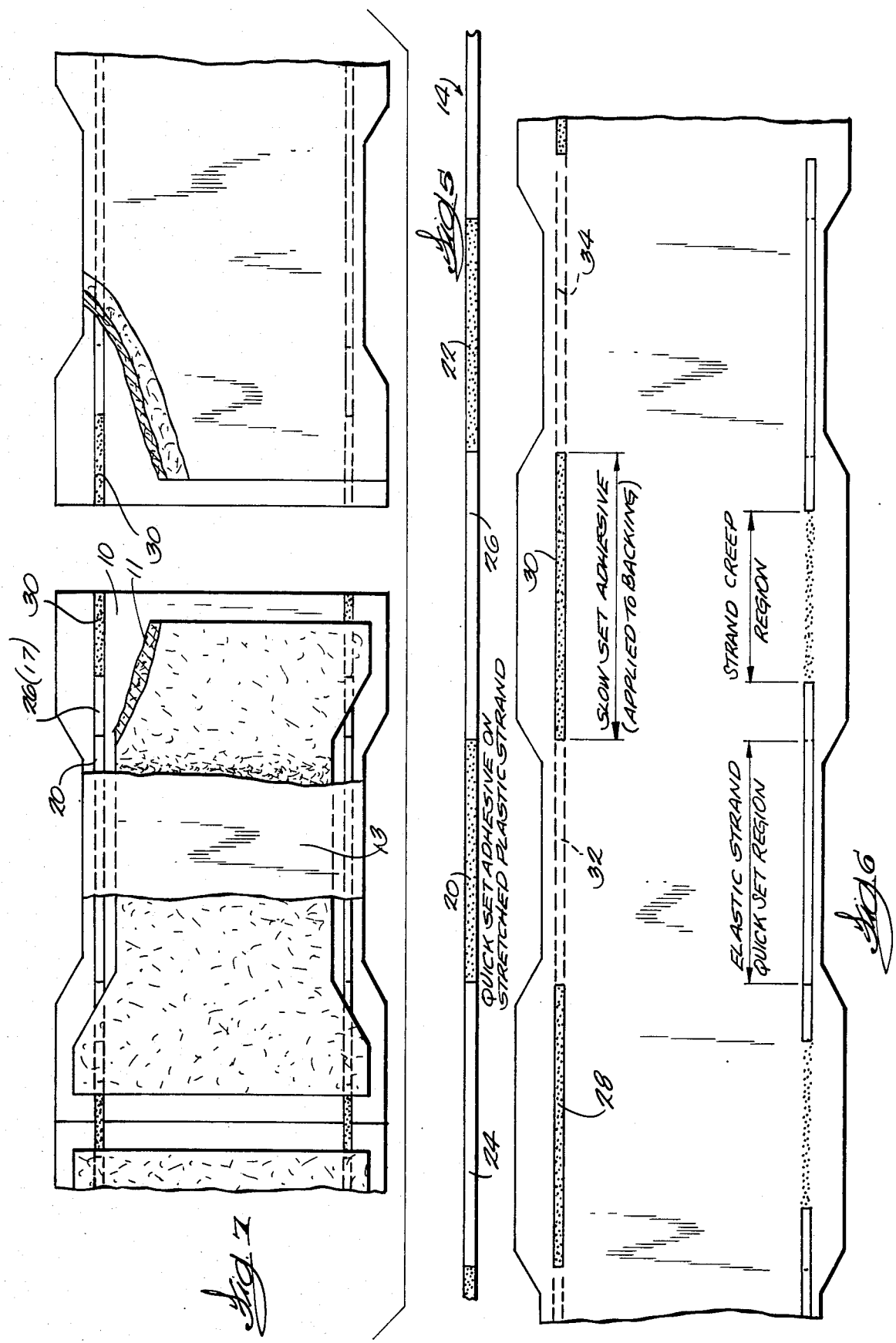

METHOD FOR SECURING ELASTIC STRANDS TO DISPOSABLE ABSORBENT ARTICLES

BACKGROUND OF THE INVENTION

This invention pertains to a method and apparatus for securing elastic strands in disposable diapers where the strands impart an elasticized characteristic to the margins of the diapers and produce a sealing effect on the body so fluids will not leak out.

One existing method of securing elastic strands in diapers is described in U.S. Pat. No. 4,081,301 which issued on Mar. 28, 1978, and names K. B. Buell as the inventor. The entire disclosure of said patent is incorporated herein by reference.

The Buell patent teaches how to fabricate disposable diapers which are elasticized in the crotch and leg contacting region of the diaper so it fits snugly around the legs of an infant. A method suggested in this patent involves feeding a continuous moisture impervious sheet and a continuous stretched elastic strand toward a diaper assembly station. A quick setting glue is applied periodically over zones on the strand which are caused to adhere to the sheet in a region that will coincide with the crotch of the infant. In the process, a pad of an absorbent material is deposited on the backing sheet and it is overlayed with a nonwoven sheet whose edges are glued to what will become the edges of the finished diaper. When the web is cut into individual diapers, since the elastic strands are stretched where they extend from one diaper to another and are without adhesive in that region, the strands snap back into the diaper where they snarl or tangle undesirably. There are four unattached snapped back elastic strand ends each of which commonly exhibits a different bunched up and tangled configuration which by no means enhances the aesthetic quality of the diaper. Some diaper manufacturers avoid this problem by applying glue continuously to the stretched elastic strand such that when the glue on the strand sets in the diaper web and the web is cut into individual diapers the strand, being set, cannot snap back into the diaper. The problem with this is that the diaper is not only elasticized in the crotch region of an infant but also up into the waist region where elasticity is not needed nor desirable.

U.S. Pat. No. 4,353,762 issued in the name of F. J. Bouda on Oct. 12, 1982, teaches applying glue continuously to the rubber strand while the strand is stretched. But the parts of the strand extending beyond the crotch region in the diaper have the glue on them deactivated by a release agent which prevents the ends of the glue coated elastic strand from sticking to the diaper backing or facing sheets. However, it is apparent when the web is cut into individual diapers, the unattached ends of the strands which extend from diaper to diaper snap back into the diaper where they can bunch up at random.

SUMMARY OF THE INVENTION

According to the invention, a pair of elastic strands are fed in parallel to a disposable diaper assembly station. In one aspect of the method, a quick setting adhesive is applied at regular periodicity to the strands so they have first zones of predetermined length with adhesive on them alternating with second zones having no adhesive. A web of inelastic material is fed concurrently to the assembly station and at the same time a relatively slower setting adhesive is applied to it at regular periodicity and in phase with the zones on the strands that are without adhesive. When the strands are superimposed upon the web with the adhesive bearing zones on the strands coincident with the zones on the web that are without adhesive and with the adhesive bearing zones on the web that are coincident with the zones on the strands that have no adhesive, the strand becomes adhered continuously to web. After consecutive diaper units are finished, the web is cut into individual diapers. The strands which formerly extended from one diaper to the next and which are tentatively held by the slow setting adhesive, then contract or creep in a straight line until all tension is relieved. The slow setting adhesive is designed to set after tension in the strand is relieved in the slow setting adhesive zone.

A more detailed description of the method and the apparatus for performing the method will now be set forth in reference to the drawings.

DESCRIPTION OF A PREFERRED EMBODIMENT

FIG. 1 is a plan view of a disposable diaper in which the elasticized parts were fabricated by the new method disclosed herein;

FIG. 2 is a side elevation diagram, of those parts of a diaper assembly line which are involved in practicing the new strand application method;

FIG. 3 is a fragment of a prior art diaper showing how an elastic strand tends to form an unsightly tangled free end on the part of the strand having no glue on it when it snaps back into the diaper after a diaper is severed from the continuous web;

FIG. 4 is a plan view of a diaper web progressing through the diaper making machine before the web reaches the station where the web is cut into individual diapers;

FIG. 5 shows a section of stretched elastic strand on which a quick setting adhesive has been applied;

FIG. 6 is a section of the diaper backing sheet part of the web on which a slower setting adhesive has been applied periodically and alternately with the adhesive being applied to the strands; and FIG. 7 illustrates how the ends of the strands contract to an untensioned condition in accordance with the invention, shortly after the diaper web is cut up into individual diapers.

DESCRIPTION OF A PREFERRED EMBODIMENT

The diaper shown in FIG. 1 is elaticized in selected regions by following the method described herein although, on first impression, the diaper appears to be conventional. It is conventional to the extent that it is comprised of a backing sheet or web of a flexible fluid impervious sheet of a material such as polyethylene. In FIG. 1 the observer is looking at the side of the diaper that interfaces with the body. The backing sheet 10 is on the side of the diaper remote from the observer. The diaper is cut away along its side margins so as to have an hourglass shape. An absorbent pad having substantially the same configuration but smaller in dimensions in all directions is imposed directly on backing sheet 10. The pad is marked 11 and extends nearly to the sides and ends of the backing sheet. The cut away regions 12 of the diaper reside in the crotch region when applied to an infant. A sheet of nonwoven material 13 is imposed over absorbent pad 11 and extends to the edges of backing sheet 10. Two elastic strands 14 and 15 are shown adhered to backing sheet 10 and between porous nonwoven facing sheet 13 and backing sheet 10. The mid regions of the elastic strands are wrinkled as is typical as the result of their being allowed to contract to a relaxed state, causing shirring of the diaper. The end regions 16 and 17 of the strands are adhered to the backing sheet in this example but they are in a completely relaxed state, that is, without tension so the end portions do not have a tendency to pull down the front and rear waist regions of the diaper when it is applied to an infant.

Refer now to FIGS. 5 and 6. FIG. 5 shows how a typical elastic strand 14 is treated in accordance with the invention. By using the apparatus in FIG. 2, the elastic strand is stretched and coated with quick setting adhesive in first zones such as 20 and 22 of predetermined length at regular periodicity. First zones alternate with second zones such as those marked 24 and 26 on which there is no adhesive. Applying adhesive periodically to elastic strands is known per se. The backing sheet or continuous web 10 of fluid impermeable material shown in FIG. 6 is concurrently coated with the apparatus in FIG. 2 with a slower setting adhesive in first zones of predetermined length such as those marked 28 and 30. The first periodic adhesive coated zones 28 and 30 on backing sheet 10 alternate with zones such as those marked 32 and 34 which are not coated with adhesive. As will be shown, when the elastic strands 14 and the backing sheet web 10 are fed towards the diaper assembly station, zones such as 20 and 22 on the strands having the quick setting adhesive are interfaced with the zones such as 32 and 34 on the backing sheet 10 to which adhesive has not yet been applied. In addition, the second zones such as 24 and 26 on the stretched elastic strand are interfaced with the first zones such as 28 and 30 on the backing sheet having the slower setting adhesive applied. The result of feeding the stretched elastic strands and taut backing sheet to the diaper assembly station concurrently with the adhesive bearing zones on each of them aligned with and in contact with the uncoated zones on the other is to cause the elastic strands to be continuously adhered to the backing sheet in an early stage of diaper fabrication.

Adhesives that can be characterized as quick setting and suitable for obtaining a permanent bond substantially upon contact between a stretched elastic strand and the backing sheet or a diaper facing sheet are well known by those involved in producing disposable diapers. Quick setting adhesives are generally of the hot melt type. A commonly used quick setting adhesive is identified as No. 995-336 and is available from Findley Adhesives Inc., Elm Grove, Wis. The relatively slow setting adhesives are usually cold water-base types although there are some commercially available hot melt types which set slowly enough to fulfill the requirements of the invention. The slow setting adhesive must remain unset at least until such time that the elastic strands are cut and the end portions have contracted to a relaxed position. However, it should be understood that the maximum setting time for the slow setting adhesive can extend beyond the time when the diapers are severed from the web all the way to the time that the diapers are packaged at the end of the production line and, even, after they are packaged. A suitable hot melt adhesive conforming to the requirements of a slow setting adhesive is one known as type X999-375-01 available from Findley Adhesives, Inc. A typical cold water-base slow setting adhesive would be one comparable to the well known type X8141-381-01 available from the same source.

FIG. 2 is a diagram of those parts of a diaper making machine involved in installing elastic strands in diapers in accordance with the invention. The absorbent pads 11 are fed to the diaper assembly region on an input conveyor belt 36. The fabricated diaper web is pulled longitudinally in a known fashion by means of pull rolls 38 toward an output station, not shown, at which the diapers severed from the webs are packaged. There are some additional sets of pull rolls, not shown, downstream in the diaper fabrication line. The pull rolls keep the web in tension until the individual diapers are severed from the web. The moisture impermeable backing sheet 10 for the diapers is fed from a parent roll, not shown, past a pair of laterally spaced apart glue discharging nozzles, one of which 40 is visible in FIG. 2. In the preferred form of the method, nozzles 40 apply the relatively slow setting adhesive periodically along the lines on the backing sheet web 10 as previously described in connection with FIG. 6. A pair of elastic strands 14 are withdrawn from a dispenser box or spool, not shown, and pass over some metering rolls, not shown, which resist having the strand drawn into the diaper fabricating machine to thereby stretch and keep the strands in tension as they pass into the machine. A suitable metering arrangement is shown in FIG. 1 of U.S. Pat. No. 4,081,031. As the strands proceed, in accordance with the preferred embodiment, periodic zones such as 20 and 22 in FIG. 5 are coated with the quick setting adhesive by means of a pair of nozzles, one of which 42 is visible in FIG. 2. At the place 44 where the elastic strands 14, 15 and the moisture impermeable backing sheet 10 become tangent to a chill roll 46, the quick setting adhesive coated zones such as 20 and 22 on the strands 14, 15 contact uncoated zones 32 and 34 on the backing sheet and the uncoated zones 24 and 26 on the strand contact the slow setting adhesive in the zones 28 and 30 with the result that the strands are adhered continuously onto the backing sheet. When the strand and backing sheet are first placed in contact, the zones on the strand having the quick setting adhesive bond tenaciously and permanently in an instant. On the other hand, the zones on the strand which interface with the slow setting adhesive, result in the two sticking together but the bond is tentative, that is, the adhesive will not set until at least some short time after the web is cut into individual diapers.

After the strands and web are adhered as just described, the composite passes a row of nozzles, one of which 48 is visible in FIG. 2. The nozzles 48 apply several parallel fine lines of glue on the backing sheet such as the lines marked 50 in FIG. 4. As the backing sheet and strand composite progress over a roll 52, the absorbent pads 11 of the diaper are deposited on the impermeable backing sheet 10. The lines of quick setting glue 50 adhere the absorbent pads to the backing sheet so that the positions of the pads are fixed relative to the edges of the backing sheet. The sheet of nonwoven material 13 which interfaces with the body of the infant wearing the diaper is fed in as shown in FIG. 2 and is adhered to backing sheet 10 around the perimeter of absorbent pad 11 by means of adhesive lines 50. A rotating bar 54 is located next to pull rolls 38. It presses down on the nonwoven facing sheet 13 to cause it to bond onto the backing sheet 10 in the regions 56 where the individual diapers will be severed from the web. The bar presses against a rotating anvil 55.

As suggested in FIG. 2, after the parts of an individual diaper are assembled in the continuously movable web, somewhere down the line a transverse cut is made across the web between consecutive diapers with a cross cut blade, not shown, located shortly after the diapers reach a folder station, not shown, which folds the left and right edges inwardly before the diapers are severed. The quick setting adhesive is set before the diapers are severed so the zones such as 20 and 22 on the stretched strand will impart elasticity to the diaper in the crotch region. In accordance with the invention, however, when the diapers are severed, the slow setting adhesive has not set as yet. The elastic strand zones between the quick setting adhesive coated zones are simply being secured tentatively to the backing sheet at this time by the slow setting adhesive so the parts of the strand on each side of the quick setting adhesive are maintained in alignment with the strands. In accordance with prior practice where adhesive was applied to the stretched strand only in zones where elasticity was to be imparted to the diaper, the spaces between these zones were without any adhesive so the ends of the strands that were unadhered were free to snap back into the diaper between the backing and facing sheets. The result was that the free ends bunch up and assume a snarled and unsightly appearance as depicted in FIG. 3. In the other prior method described in U.S. Pat. No. 4,353,762 where quick setting adhesive is applied to the entire length of the stretched elastic strand but a release agent is applied intermittently, the same result can occur. That is, when the diapers are severed, the unadhered ends with the release agent are free to snap into the diaper and wad up as suggested in FIG. 3.

In practicing the invention it is found most desirable to cut the elastic strands at the mid-line between successive diapers before the diapers are severed individually from the web so the web will be under tension when the strands are cut. To achieve this a pair of laterally spaced apart rotating blades are provided. The blade 57 in the forefront in FIG. 2 is visible and its mate is behind it. The blades act against a rotating anvil 58. The blades make two slits through the web in a zone such as 56 when the web passes blades 57 to thereby cut through the elastic strands 14 and 15. The slits are marked 59 and 60 in FIG. 4. At the moment the strands are slit in a zone where they are tentatively stuck with slow setting adhesive, the strands begin to contract. The advantage of pre-cutting the strands is that the strands can begin contracting while the web is still under tension. This minimizes the possibility of the diapers skewing after being cut off as a result of the elastic on one side contracting at a faster rate than the elastic on the opposite side. Recognize, however, that precutting the strands requires use of an even quicker setting quick setting adhesive, since the cut-off point will be much closer to the adhesive application zone in most diaper making machines.

FIG. 7 shows what happens immediately after the individual diapers are severed from the web in a case where the elastic strands are installed in the diaper by the method of the present invention. The quick setting adhesive zone 20 of the elastic strand that imparts elasticity to the mid region of the diaper is set already. The part of the strand 26 that was placed in contact with the slow setting adhesive will be allowed to contract to the condition in which it is shown. In other words, the elastic strand zones 26 creep along the tentatively adhered slow setting adhesive coated zones 30 before the slow setting adhesive has enough time to set. In due course, when the slow setting adhesive has set, the end zone 26 of the strand will be totally relaxed and unstretched but permanently fixed in a straight line with the remainder of the strand.

In the foregoing discussion, the principles of the invention were demonstrated in the case where quick setting adhesive is applied periodically to the elastic strands and slower setting adhesive is applied in alternate periodicity to the backing sheet. It is, however, within the scope of the invention to do the method oppositely, that is, to apply the slow setting adhesive periodically to the elastic strands and the quick setting adhesive to the backing sheet in alternate periodicity.

Although an embodiment of the invention has been described in detail, such description is intended to be illustrative rather than limiting, for the invention may be variously emobodied and is to be limited only by construing the claims which follow.

I claim:

1. A method for attaching elastic strands continuously to a moving inelastic web of interconnected articles to impart an elasticized characteristic to predetermined regions on the individual articles and to leave other regions in said articles without elasticized characteristics, said method comprising the steps of:

feeding an elastic strand in a stretched condition and a continuous sheet of material concurrently toward an article assembly station, applying a quick setting adhesive periodically to zones of predetermined length on a selected one of the strand or the sheet and applying a relatively slower setting adhesive periodically to zones of predetermined length on the other of the strand or the sheet while said strand and sheet are being fed, causing said stretched strand and said sheet to contact in a relationship such that zones having quick setting adhesive alternate with zones having the slower setting adhesive so said strand becomes adhered continuously to said sheet and the zones having the slow setting adhesive are tentatively adhered and extend from one of said interconnected articles to the next, maintaining said elastic strand in a stretched condition at least until said quick setting adhesive sets, after the articles have passed said assembly station and before said slower setting adhesive sets cutting said elastic strand transversely to the line of movement of the sheet at a place between successive articles across which place said tentatively adhered zone extends, cutting of said strand allowing the tentatively adhered ends of the strand to contract to an unstretched condition before said slow setting adhesive sets such that after it sets said ends are adhered but do not impart an elastic characteristic to the region of the article to which said ends adhere.

2. The method according to claim 1 including cutting said sheet transversely coincidentally with cutting said elastic strand transversely.

3. The method according to claim 1 wherein said quick setting adhesive is applied to said stretched elastic strand and said relatively slower setting adhesive is applied to said sheet.

4. The method according to claim 1 wherein said quick setting adhesive is applied to said sheet and said slow setting adhesive is applied to said elastic strand.

5. The method according to any one of claims 1, 2, 3 or 4 wherein said quick setting adhesive sets before the elastic strands are cut.

6. The method according to any one of claims 1, 2, 3 or 4 wherein said slower setting adhesive sets after the elastic strands have been cut and the end portions of the strands have contracted to a relaxed condition.

7. The method according to claim 3 wherein said quick setting adhesive is a hot melt adhesive and said slower setting adhesive is a cold water base adhesive.

* * * * *